United States Patent
Morrison et al.

(10) Patent No.: US 6,320,193 B1
(45) Date of Patent: Nov. 20, 2001

(54) METHOD FOR NON-INTRUSIVELY IDENTIFYING A CONTAINED MATERIAL UTILIZING UNCOLLIDED NUCLEAR TRANSMISSION MEASUREMENTS

(75) Inventors: John L. Morrison, Idaho Falls; Alan G. Stephens, Shelley; S. Blaine Grover, Idaho Falls, all of ID (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 09/259,418

(22) Filed: Feb. 26, 1999

(51) Int. Cl.[7] .................................................. G01N 23/10
(52) U.S. Cl. ...................... 250/393; 250/395; 250/358.1; 378/53
(58) Field of Search ............................... 250/393, 390.04, 250/390.06, 391, 395, 358.1; 378/53, 54, 56, 57

(56) References Cited

U.S. PATENT DOCUMENTS

| | | | |
|---|---|---|---|
| H1097 | * 8/1992 | Burnham et al. | 378/207 |
| 4,200,792 | * 4/1980 | Fanger et al. | 250/359 |
| 4,228,351 | * 10/1980 | Snow et al. | 378/54 |
| 4,618,975 | * 10/1986 | Glantschnig | 378/51 |
| 4,837,442 | 6/1989 | Manglos . | |
| 4,864,142 | 9/1989 | Gomberg . | |
| 5,076,993 | 12/1991 | Sawa et al. . | |
| 5,098,640 | 3/1992 | Gozani . | |
| 5,132,998 | * 7/1992 | Tsutsui et al. | 378/98.9 |
| 5,296,712 | 3/1994 | Swanson . | |
| 5,446,288 | 8/1995 | Tumer . | |
| 5,479,023 | 12/1995 | Bartle . | |
| 5,524,133 | * 6/1996 | Neale et al. | 378/53 |
| 5,600,700 | * 2/1997 | Krug et al. | 378/57 |
| 5,818,054 | 10/1998 | Randers-Pherson et al. . | |

OTHER PUBLICATIONS

Presentation entitled, "A Neutron Transmission Measurement to Identify chemical Agent in Chemical Munitions", given by John L. Morrison in Mar. 1998.

\* cited by examiner

Primary Examiner—Constantine Hannaher
Assistant Examiner—Albert Gagliardi
(74) Attorney, Agent, or Firm—Bradley W. Smith; Mark P. Dvorscak; Virginia B. Caress

(57) ABSTRACT

An improved nuclear diagnostic method identifies a contained target material by measuring on-axis, mono-energetic uncollided particle radiation transmitted through a target material for two penetrating radiation beam energies, and applying specially developed algorithms to estimate a ratio of macroscopic neutron cross-sections for the uncollided particle radiation at the two energies, where the penetrating radiation is a neutron beam, or a ratio of linear attenuation coefficients for the uncollided particle radiation at the two energies, where the penetrating radiation is a gamma-ray beam. Alternatively, the measurements are used to derive a minimization formula based on the macroscopic neutron cross-sections for the uncollided particle radiation at the two neutron beam energies, or the linear attenuation coefficients for the uncollided particle radiation at the two gamma-ray beam energies. A candidate target material database, including known macroscopic neutron cross-sections or linear attenuation coefficients for target materials at the selected neutron or gamma-ray beam energies, is used to approximate the estimated ratio or to solve the minimization formula, such that the identity of the contained target material is discovered.

9 Claims, 2 Drawing Sheets

METHOD FOR NON-INTRUSIVELY IDENTIFYING A CONTAINED MATERIAL UTILIZING UNCOLLIDED NUCLEAR TRANSMISSION MEASUREMENTS

The United States Government has right in this invention pursuant to Contract Number DE-AC07-94ID13223 between the United States Government and Idaho National Environmental and Engineering Laboratory, as represented by Lockheed Martin Idaho Technologies Company.

TECHNICAL FIELD

The present invention relates to nuclear densitometry, and, in particular, to a method for non-intrusively identifying a target material enclosed within a container by detecting on-axis, uncollided radiation transmissions of mono-energetic penetrating radiation through the container at first and second radiation beam energies, and applying developed algorithms to estimate either an identifying ratio or to solve an identifying minimization formula, wherein the ratio and the minimization formula are based on characteristic macroscopic neutron cross-sections or linear attenuation coefficients for the target material at the first and second neutron or gamma-ray beam energies, respectively.

BACKGROUND OF INVENTION

Diagnostic nuclear techniques generally involve the use of highly penetrating radiation comprised of nuclear particles to identify a concealed or unknown target material by detecting and measuring the interaction between the nuclear particles of the penetrating radiation and the target material nuclei, and analyzing the absorptive and/or scattering patterns that result from the interaction. For example, Thermal Neutron Activation (TNA) and Fast Neutron Activation (FNA) are neutron transmission techniques for identifying a target material by measuring the spectrum of gamma rays emitted from the target material, as a result of neutron bombardment and the subsequent absorption of neutrons by the target material. Thermal and Fast Neutron Activation methods are characterized by the energy level of the interrogating neutron beam, i.e., TNA uses a neutron beam having a low energy of about 0.025 eV, while FNA involves a very high energy neutron beam of about 14 MeV.

Although a beam of penetrating radiation transmitted through a target material may interact with the target material nuclei to produce identifiable signatures, a number of the nuclear particles comprising the penetrating radiation may also have no interaction with the target material nuclei, such that they pass through the target material, maintaining their initial speed and trajectory. The intensity of the non-interacting or uncollided radiation flux exiting the target material is less than the initial beam intensity, diminished by the fraction of interacting nuclear particles, either absorbed or scattered. For a neutron transmission, the measurement of the number of uncollided neutrons per unit time is quantified as the uncollided neutron flux or intensity, I. Analogously, the detection and measurement of the number of non-interacting photons per unit time, resulting from interrogation of the target material by a gamma-ray beam, is quantified as the uncollided gamma-ray flux or intensity, I.

With respect to neutron transmission measurements, each chemical element has a microscopic parameter, referred to as the neutron cross-section, that represents the probability of a neutron interaction with a nucleus of the target material, depending upon the velocity of the neutron. The sum of the cross-sections at a given neutron velocity is the total microscopic neutron cross-section, expressed in units of effective target area per atom ($cm^2$/atom). The corresponding macroscopic neutron cross-section ($cm^2$/$cm^3$) is the product of the total microscopic cross-section ($cm^2$/atom) and the atomic density of the target material (atoms/$cm^3$). For a chemical compound composed of n different elements, the macroscopic neutron cross-section $\Sigma_C$ is described by Equation (1), and Equation (2) is an expression of the molecular density for a compound, C.

$$\Sigma_C = N_C \sum_{i=1}^{n} v_i \sigma_i \qquad (1)$$

$$N_C = N \left( \frac{\rho}{MW} \right)_C \qquad (2)$$

where $\Sigma_C$ is the total macroscopic neutron cross-section for compound C;

$N_C$ is the molecular density, molecules of compound C/$cm^3$;

N is Avogadro's number (6.02e23 molecules/gm mole);

$v_i$ is the number of atoms of element i per molecule of compound C; and $\sigma_i$ is the total microscopic neutron cross-section for element i at a given neutron velocity.

Tables I and II below list physical characteristics of six chemical agents and their neutron kinetic energy dependence ($\frac{1}{2}$ $MV^2$), respectively.

TABLE I

Physical Characteristics of Selected Chemical Agents

| Agent | Type | Chemical Formula | Molecular Weight | Density | Mass Attenuation Coefficient |
|-------|------|------------------|------------------|---------|------------------------------|
| GB | Nerve | $C_4H_{10}O_2PF$ | 140.1 | 1.09 | 0.159 |
| GA | Nerve | $C_5H_{11}O_2PN_2$ | 162.3 | 1.07 | 0.156 |
| GD | Nerve | $C_7H_{16}O_2PF$ | 182.2 | 1.02 | 0.151 |
| VX | Nerve | $C_{11}H_{26}O_2PSN$ | 267.4 | 1.008 | 0.152 |

TABLE II

Neutron Kinetic Energy Dependence of Selected Chemical Agents

| Energy keV | $\sigma_{GA}$ $cm^2$/mol | $\Sigma_{GA}$ $cm^2$/$cm^3$ | $\sigma_{GB}$ $cm^2$/mol | $\Sigma_{GB}$ $cm^2$/$cm^3$ | $\sigma_{GD}$ $cm^2$/mol | $\Sigma_{GD}$ $cm^2$/$cm^3$ | $\sigma_{VX}$ $cm^2$/mol | $\Sigma_{VX}$ $cm^2$/$cm^3$ |
|---|---|---|---|---|---|---|---|---|
| 150 | 0.596 | 0.63772 | 0.609 | 0.66381 | 0.728 | 0.74256 | 0.789 | 0.79689 |
| 220 | 0.513 | 0.54891 | 0.528 | 0.57552 | 0.63 | 0.6426 | 0.677 | 0.68377 |
| 272 | 0.475 | 0.50625 | 0.525 | 0.57225 | 0.596 | 0.60996 | 0.643 | 0.64943 |
| 350 | 0.433 | 0.46331 | 0.464 | 0.50576 | 0.541 | 0.55182 | 0.559 | 0.56459 |

TABLE II-continued

Neutron Kinetic Energy Dependence of Selected Chemical Agents

| Energy keV | $\sigma_{GA}$ cm²/mol | $\Sigma_{GA}$ cm²/cm³ | $\sigma_{GB}$ cm²/mol | $\Sigma_{GB}$ cm²/cm³ | $\sigma_{GD}$ cm²/mol | $\Sigma_{GD}$ cm²/cm³ | $\sigma_{VX}$ cm²/mol | $\Sigma_{VX}$ cm²/cm³ |
|---|---|---|---|---|---|---|---|---|
| 450 | 0.477 | 0.51039 | 0.511 | 0.55699 | 0.557 | 0.56814 | 0.555 | 0.56055 |
| 550 | 0.346 | 0.37022 | 0.382 | 0.39458 | 0.428 | 0.43656 | 0.451 | 0.45551 |
| 660 | 0.324 | 0.34666 | 0.334 | 0.36408 | 0.393 | 0.40086 | 0.415 | 0.41915 |
| 750 | 0.302 | 0.32314 | 0.319 | 0.34771 | 0.373 | 0.38048 | 0.391 | 0.39491 |
| 850 | 0.283 | 0.30281 | 0.299 | 0.32591 | 0.35 | 0.357 | 0.367 | 0.37067 |
| 1000 | 0.31 | 0.3317 | 0.323 | 0.35207 | 0.358 | 0.36516 | 0.366 | 0.36968 |

For distance δx within compound C, the probability of a neutron-nucleus collision is Σδx, provided that this product is much less than one (<<1.0). The probability that a neutron travels distance $X_C$ without undergoing an interaction is a Posison distribution described by $e^{-\Sigma_C X_C}$. If a neutron beam passes in series through m sucessive compounds, then the probability of zero neutron-nucleus interactions occurring over the total path length is described by Equation (3).

$$e^{-\sum_{j=1}^{m}\Sigma_j x_j} \quad (3)$$

Finally, the uncollided neutron intensity, I, is represented in the attenuation equation, Equation (4).

$$I = \varepsilon \frac{A_d}{4\pi R^2} S_0 e^{-\sum_{j=1}^{m}\Sigma_j x_j} \quad (4)$$

where ε is the detector efficiency at the original neutron velocity, representing the fraction of uncollided neutrons at a certain velocity that produce counted pulses;

$S_o$ is the source strength of neutrons per second, at a certain velocity, emitted in all directions;

$$\frac{A_d}{4\pi R^2}$$

is the solid angle subtended by a detector of sensitive area $A_d$ located at a distance R from the point source, representing the fraction of $S_o$ neutrons leaving the source in a direction toward the detector; and $e^{-\Sigma_j x_j}$ is the fraction of uncollided neutrons incident on the detector area $A_d$.

An analogous attenuation equation describes the uncollided gamma-ray intensity from gamma-ray transmissions, except that the variable $\Sigma_C$, the total macroscopic neutron cross-section for compound C, is replaced by the variable $\mu_C$, the linear attenuation coefficient for compound C. The gamma-ray linear attenuation coefficient is a function of the compound's molecular structure and the gamma photon energy.

Importantly, where the parameters of Equation (4) are known, a measurement of the uncollided neutron intensity, I, allows calculation of the macroscopic neutron cross-section for the compound, $\Sigma_C$. Since the macroscopic neutron cross-section, $\Sigma_C$, is unique to each compound, the compound is identifiable by the calculation of $\Sigma_C$. Alternatively, measurement of the uncollided gamma-ray beam intensity, I, allows calculation of the linear attenuation coefficient, $\mu_C$, an identifying characteristic unique to each compound.

Unfortunately, defining the parameters of the attenuation equation, Equation (4), to enable calculation of $\Sigma_C$ or $\mu_C$ is difficult, since the parameters are largely dependent on geometry. In addition, where the target material, for example, is a chemical agent contained within a chemical munition made of a thick steel shell, the use of neutron transmission measurements to identify the chemical agent becomes more complex, and the sensitivity of the gamma radiation to the chemical agent sharply decreases, as high energy gamma-ray beams are required to penetrate the steel shell.

A need exists in the art for a safe nuclear diagnostic technique that non-intrusively identifies contained materials without relying on the geometry of the system. Furthermore, it is desirable for the nuclear diagnostic technique to be non-complex, non-time consuming, highly sensitive, reliable, and accurate, with an increased probability of correct detection and a decreased probability of false alarms.

The present invention is an improved nuclear diagnostic method for identifying a contained target material, involving the steps of measuring on-axis, mono-energetic uncollided radiation transmitted through a target material for two penetrating radiation beam energies, and applying specially developed algorithms to estimate a ratio of macroscopic neutron cross-sections for the uncollided radiation at the two energies, where the penetrating radiation is a neutron beam, or a ratio of linear attenuation coefficients for the uncollided radiation at the two energies, where the penetrating radiation is a gamma-ray beam. Alternatively, the measurements are used to derive a minimization formula based on the macroscopic neutron cross-sections for the uncollided radiation at the two neutron beam energies, or the linear attenuation coefficients for the uncollided radiation at the two gamma-ray beam energies. A candidate target material database, including known macroscopic neutron cross-sections or linear attenuation coefficients for target materials at the selected neutron or gamma-ray beam energies, is used to approximate the estimated ratio or to solve the minimization formula, such that the identity of the chemical agent is discovered.

A feature of the present nuclear diagnostic technique is that the method is performed independent of the geometry of the material containment system, such that the successive path lengths of the radiation transmissions through various compounds comprising the target material is not a factor in the identification process. The improved method accomplishes accurate and reliable measurements, providing identification within minutes.

Therefore, in view of the above, a basic object of the present invention is to provide an improved nuclear diagnostic technique for non-intrusively identifying contained materials, e.g., chemical agents, irrespective of the individual path lengths of the penetrating radiation through the container and the enclosed chemical agent.

Another object of the present invention is to provide an improved neutron transmission method for identifying a contained material by estimating a macroscopic neutron cross-section ratio for the contained material, using on-axis, uncollided neutron transmission measurements at two neutron beam energies.

Another object of the present invention is to provide an improved neutron transmission method for identifying a contained material by solving a minimization formula based on macroscopic neutron cross-sections for the contained material, using on-axis, uncollided neutron transmission measurements at two neutron beam energies.

Another object of the present invention is to provide an improved gamma-ray transmission method for identifying a contained material by estimating a linear attenuation coefficient ratio for the contained material, using on-axis, uncollided photon measurements at two gamma-ray beam energies.

Another object of the present invention is to provide an improved neutron transmission method for identifying a contained material by solving a minimization formula based on linear attenuation coefficients for the contained material, using on-axis, uncollided photon measurements at two gamma-ray beam energies.

Yet a further object of the present invention is to provide an improved and environmentally safe nuclear diagnostic technique that has a high probability of detection and a low probability of false alarms, a simplified design, a rapid response time, an improved signal-to-noise ratio, and discrete emissions of radiation.

Additional objects, advantages, and novel features of the invention will be more fully understood from the following description of the invention, and/or will become apparent to those skilled in the art upon examination of the following description and/or by practice of the invention.

BRIEF SUMMARY OF THE INVENTION

Briefly, this invention is a method for non-intrusively identifying a target material enclosed within a container by measuring the transmission of on-axis, mono-energetic, uncollided radiation through the container at two or more radiation beam energies, and applying developed algorithms either to estimate an identifying ratio of the macrocopic neutron cross-sections of the target material at two energies, where the interrogating beam is a neutron beam, or an identifying ratio of the linear attenuation coefficients of the target material at two energies, where the interrogating beam is a gamma-ray beam, or, alternatively, to solve a minimization formula based on the macroscopic neutron cross-sections or the linear attenuation coefficients of the target material at the two neutron or gamma-ray beam energies, respectively, such that determining the best solution to the minimization formula identifies the target material.

The method assumes that the measurement of uncollided nuclear transmissions is one-dimensional (i.e., the beam of penetrating radiation and the resulting uncollided radiation travels along the same, approximately linear path from the beam source to the detector, referred to as the transmission path); the penetrating radiation is mono-energetic; uncollided radiation is accurately detected in the presence of measurement contamination from scattered lower energy radiation; and the total length of the transmission path rough the subject under interrogation, e.g., through the container and the target material enclosed therein, is known. In addition, the identity and the macroscopic neutron cross-section or linear attenuation coefficient of the material(s) comprising the container is measured or known.

Several embodiments of the present method are described with respect to the identification of a chemical agent contained within the steel shell of a chemical munition.

In the first embodiment, two sets of uncollided neutron transmission measurements are performed. The first set of measurements involves performing an on-axis transmission of a mono-energetic neutron beam along a selected transmission path through the chemical munition, such that the beam passes through a void space (e.g., air bubble) within the steel shell, at two selected neutron beam energies. The second set of measurements involves re-orientating the chemical munition, such that the neutron beam is transmitted along the same transmission path through the chemical munition, however, the transmission path now passes through the chemical agent (CA), and measuring the uncollided neutron flux at the same two neutron beam energies. A Two Energy Void/CA Algorithm is used to isolate the macroscopic neutron cross-sections for uncollided neutron transmissions through the chemical agent (CA) only, at the selected neutron energies, and to estimate the ratio of the CA macroscopic neutron cross-sections, such that a database of known macroscopic neutron cross-sections for candidate chemical agents at the selected neutron energies determines the identity of the contained chemical agent.

In a second embodiment, only a single set of uncollided neutron transmission measurements is required, such that measurements through a void space or re-orientation of the chemical munition is unnecessary. On-axis, mono-energetic neutron transmissions are conducted along a selected transmission path through the chemical munition, including the chemical agent, at two selected neutron beam energies, such that the transmission path has a total path length that includes the path length through the steel shell and the path length through the contained chemical agent (CA), and a Two Energy CA Algorithm is used to derive a minimization formula for identifying the chemical agent. The Two Energy CA Algoritm incorporates the total path length relationship to eliminate unknown variables from the minimization formula, such that candidate chemical agents and their corresponding macroscopic neutron cross-sections at the selected neutron energies are successively evaluated in the minimization formula to determine a solution, or best fit, resulting in identification of the contained chemical agent.

In a third embodiment, only a single set of uncollided neutron transmission measurements is required, and void space measurements or chemical munition re-orientation is unnecessary. On-axis, mono-energetic neutron transmissions are conducted along a selected transmission path through the chemical munition, including the chemical agent, at two selected neutron beam energies, such that the transmission path has a total path length that includes the path length through the steel shell and the path length through the contained chemical agent (CA), and a Modified Two Energy CA Algorithm is used to identify the contained chemical agent by incorporating the total path length relationship to estimate a ratio of relative macroscopic neutron cross-sections of the chemical munition less the steel shell, at the two neutron energies. A database of known macroscopic neutron cross-sections for candidate chemical agents, as well as for steel, at the selected neutron energies, is used to calculate a matching relative ratio for identifying the contained chemical agent.

Each of the above described embodiments, involving uncollided neutron transmission measurements, correspond to analogous embodiments that identify the contained material by gamma-ray transmission measurements. For the analogous embodiments, mono-energetic gamma-ray beams are transmitted through the chemical munition along a selected linear transmission path, and on-axis detection of non-interacting photon particles is performed for two gamma-ray beam energies. The Two Energy Void/CA Algorithm, Two Energy CA Algorithm, or Modified Two Energy CA Algorithm, described above, are adapted to the gamma-ray transmission measurements and applied to estimate an identifying ratio or relative ratio of the linear attenuation coefficients of the target material at the two gamma-ray beam energies, or to solve an identifying minimization formula based on the linear attenuation coefficients of the target material at the two gamma-ray beam energies.

In a fourth and final embodiment, two sets of uncollided neutron transmission measurements are performed and a High Precision Two Energy CA Algorithm is applied. The first set of measurements involves on-axis, mono-energetic neutron transmissions conducted along a selected transmission path through the chemical munition, including the chemical agent (CA), at a first selected base neutron energy and a first selected perturbated neutron energy. The second set of measurements involves on-axis, mono-energetic neutron transmissions conducted along the same selected transmission path through the chemical munition, including the chemical agent, at a second base neutron beam energy and a second perturbated neutron beam energy. The High Precision Two Energy CA Algorithm augments the Two Energy CA Algorithm of the second embodiment of the invented method, by incorporating Taylor Series concepts, and produces a minimization formula that approximates the identity of the chemical agent with higher precision.

The fourth embodiment is not practically adapted to gamma-ray transmission measurements, as the energy of the gamma-ray beam is not amenable to slight adjustments.

BRIEF DESCRIPTION OF THE DRAWINGS

The appended claims set forth those novel features which characterize the invention, however, the invention, as well as further objects and advantages thereof, will best be understood by reference to the following detailed description of a preferred embodiment, in conjunction with the accompanying drawings, where like reference characters identify like elements throughout the various figures, in which:

DETAILED DESCRIPTION OF THE INVENTION

The present invention relates to an improved nuclear diagnostic method for non-intrusively identifying a target material enclosed within a container. The improved method generally involves interrogating the container with two mono-energetic penetrating beams of radiation at two selected beam energies, measuring the uncollided radiation flux with an on-axis detector, applying an algorithm either to estimate a ratio of macroscopic neutron cross-sections or linear attenuation coefficients for target material at the two energies, or to derive a minimization formula incorporating the macroscopic neutron cross-sections or linear attenuation coefficients for target material at the two selected energies, and utilizing a database of macroscopic neutron cross-sections or linear attenuation coefficients for candidate target materials at the selected energies to either approximate the ratio or solve the minimization formula, thereby discovering the identify the target material.

A feature of the present method is application of algorithms that are ultimately independent of the geometry of radiation detector angles, as well as the individual path lengths of the penetrating radiation transmissions through container, such that problematic variables appearing in prior art systems, are effectively eliminated.

All embodiments of the present method are based on the following general assumptions. The measurement of uncollided nuclear transmissions is one-dimensional, such that the penetrating radiations and resulting measured uncollided radiations essentially travel along the same, approximately linear path from the beam source to the detector, referred to as the transmission path. The total path length of the transmission path through the subject under interrogation is measured and known, e.g., a measured width at a selected cross-section of a chemical munition. The interrogating or penetrating radiation is mono-energetic and may be either a mono-energetic neutron or gamma-ray beam. The uncollided particle radiation, e.g, uncollided neutrons or non-interacting photons, are accurately detected in the presence of measurement contamination from scattered, lower energy radiation.

Where the subject under interrogation is a contained material, the identity and the macroscopic neutron cross-section or the linear attenuation coefficient of the material(s) comprising the container is measured or known.

The method is described with respect to a munition containing a chemical agent, however, the method is not limited to this application, but may be used in any application where the on-axis detection of an uncollided radiation flux for a mono-energetic beam of penetrating radiation is possible. The method may be employed to detect any contained material, including explosives, drugs, contraband, etc., contained within dense, thick walled, multi-layered, and/or sealed containers.

Figure 1:
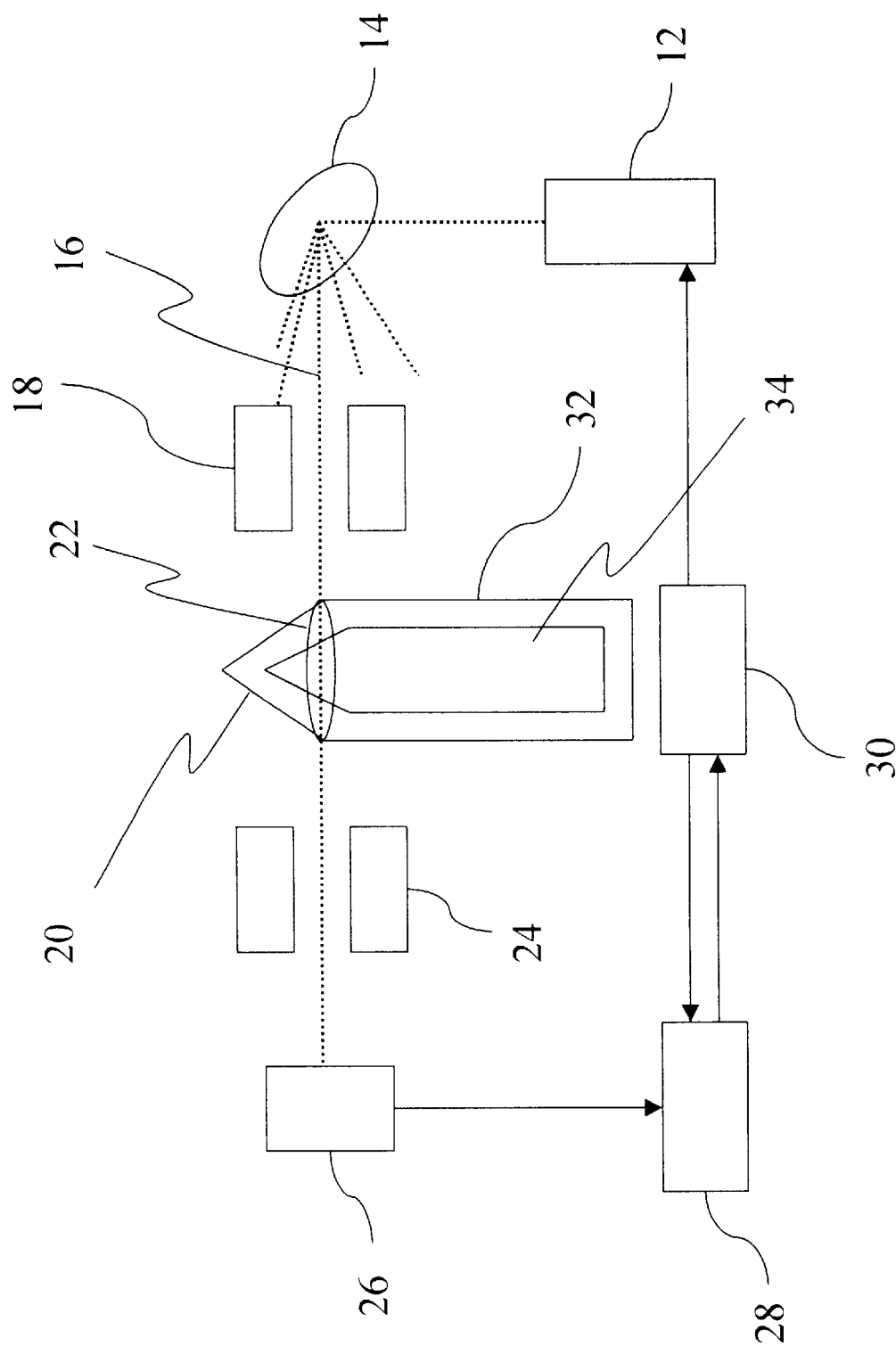
FIG. 1 shows an apparatus designed to accomplish the embodiments of the present method, involving uncollided neutron transmission measurements.

FIG. 1 illustrates an apparatus designed to accomplish the embodiments of the present method that involve an interrogating mono-energetic neutron beam and on-axis detection of the uncollided neutron flux. A relatively mono-energetic beam of neutrons 16 is generated by a proton accelerator 12 and a neutron generating target 14 (e.g., a Van de Graaff accelerator, a tritium target). Adjustment of the accelerator voltage determines the energy of the neutrons, preferably in the fast neutron energy range of between about 100 keV and about 1000 keV. A first neutron collimator 18 is positioned between the neutron generating target 14 and the target material subject to interrogation, e.g., a chemical munition 20, for reducing the population of scattered neutrons, and a second neutron collimator 24 is positioned between the chemical munition 20 and an on-axis neutron detector 26, for collimating the neutron beam 16 exiting the chemical munition 20 and shielding the detector from scattered neutrons.

The chemical munition 20, including a shell-shaped container 32 defining a chemical agent containment area 34, is disposed in the transmission path of neutron beam 16, such that the neutron beam is transmitted through the chemical munition 20 along a specified and approximately linear path at a certain cross-section of the chemical munition 20. Thus, whereas various transmission path lengths through different materials comprising the chemical munition 20 are unknown, a physical, exterior measurement of the chemical munition 20 provides the total path length of a radiation transmission through the chemical munition 20 along the specified linear path at the cross-section 22.

The neutron detector 26 is capable of distinguishing uncollided, mono-energetic neutrons from gamma radiation and lower energy scatter neutrons, and is preferably a shielded proton recoil detector. The neutron detector 26 counts the number of uncollided neutrons that pass through the chemical munition 20 without interacting with the nuclei of atoms in its path, expressed as the number of uncollided neutrons per unit time or the uncollided neutron intensity, I. The uncollided neutrons approximately travel along the one-dimensional path through the cross-section 22 of the chemical munition 20 with the same neutron energy as the neutrons comprising the initial, generated neutron beam. The neutron detector 26 is essentially on-axis with the neutron generating target 14, and directly intersects the transmission path of the neutron beam 16 and uncollided neutrons. A low energy neutron shield may be incorporated into the detection system (not shown), to permit filtering of neutrons striking the front face of the detector only, such that low energy, scattered neutrons are not detected.

Any neutron detection system providing an accurate response to the uncollided neutron flux and discrimination between uncollided neutrons and neutron induced gamma radiation and/or lower energy scattered neutrons is appropriate, e.g., a liquid scintillation detector with discrimination electronics and shielding to reject gamma radiation; a 4-atm$^3$He neutron detector enclosed within a ½ inch polyethylene liner and a borated metal ($^{10}$B) neutron filter.

The neutron detector 26 transfers information to a signal analyzer 28 that communicates with a data system 30. The data system 30 is also in communication with the proton accelerator 12. The data system acquires the pulse data from detector amplifiers (not shown) and a neutron energy spectra is obtained. The apparatus is operable at high and low energies and utilizes standard electronics. Calibration of the system is performed prior to positioning the target material in the path of the penetrating beam of radiation.

Figure 2:
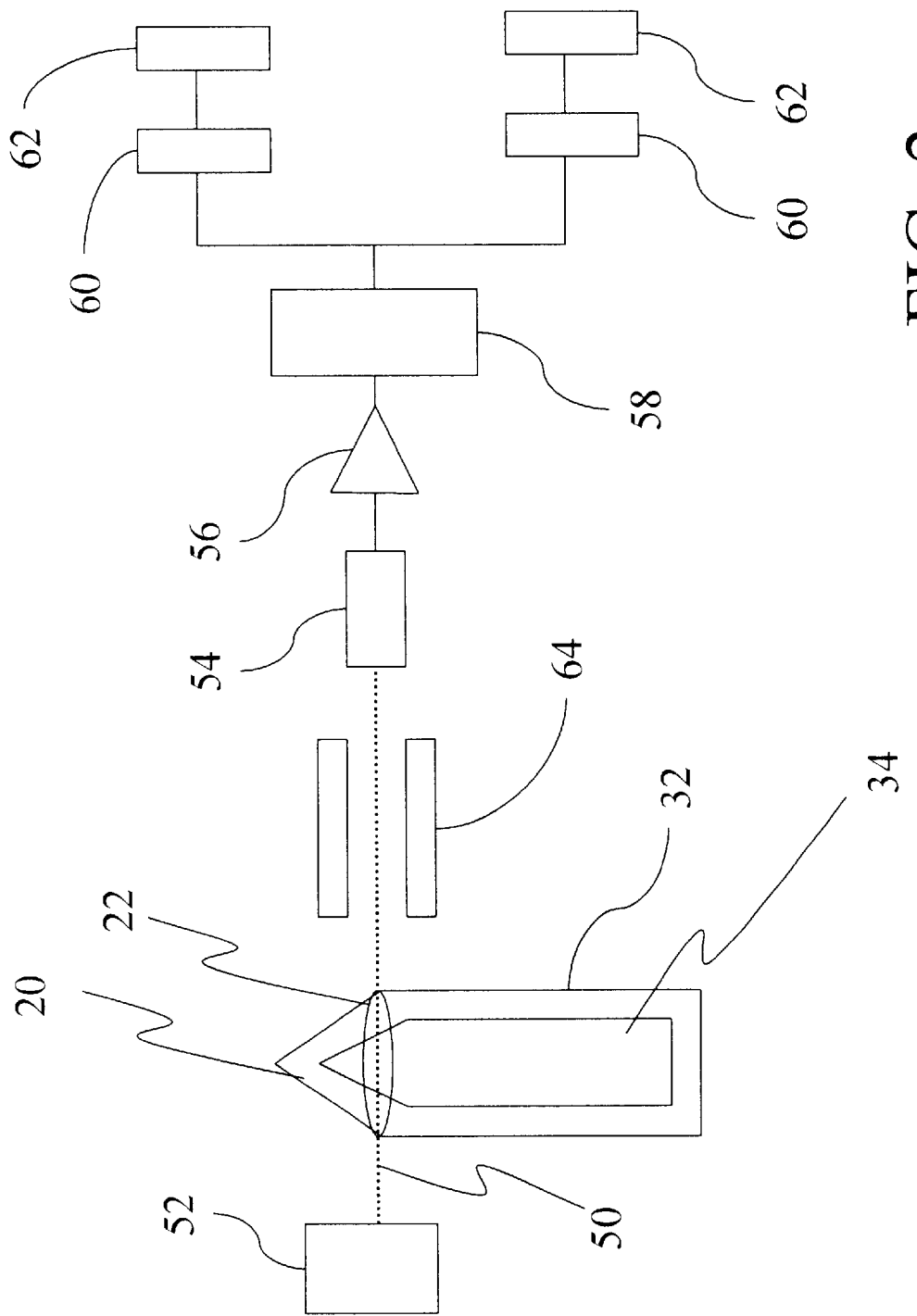
FIG. 2 shows an apparatus designed to accomplish the analogous embodiments of the present method, involving non-interacting photon transmission measurements.

For the embodiments of the present invention in which a gamma-ray beam interrogates the chemical munition 20, rather than a neutron beam, FIG. 2 illustrates an apparatus designed for generating an interrogating mono-energetic gamma-ray beam at two selected energies, and detecting non-interacting photons. A two photon gamma source 52 is provided for generating a beam of gamma radiation 50 at first and second energies. A scintillation detector 54, preferably including a NaI scintillation detector, a preamplifier 56, and a main amplifier 58, is positioned on-axis with the two photon gamma source 52 and detects non-interacting photons, i.e., photons that pass through the target material without interacting with target material nuclei, converting the detected photons to voltage pulses with an amplitude proportional to the photon energy. The photon pulses are paralleled into two single channel analyzers (SCAs) 60, the first tuned to detect the transmitted gamma beam at the first energy level and the second tuned to detect the transmitted gamma beam at the second energy level. A count rate meter 62 is dedicated to each SCA to count the pulses from the SCA over a predetermined period of time. A collimator 64 is provided to collimate the gamma beam and reduce sensitivity to scattered gamma radiation.

The target material selected as a non-limiting example for descriptive purposes is a chemical munition 20, including a thick shell 32 virtually transparent to the penetrating radiation (e.g., neutron beam or gamma-ray beam), and a chemical agent containment area 34 defined by the shell and containing an unknown chemical agent. The composition of the shell is known, and in this case is steel. A physical measurement of the transmission path of penetrating radiation through the chemical munition 20 at the selected cross-section 22 is performed, such that the measurement represents the total path length for radiation transmitted through the chemical munition, including the path length of the neutron beam through the steel shell $X_s$ (unknown) and path length of the neutron beam through the chemical agent containment area $X_c$ (unknown). Thus, the geometry for an uncollided neutron transmission measurement, I, through the chemical munition 20 is assumed to be approximately one-dimensional and linear, having a measured total path length, $D=X_s+X_c$. Importantly, a one-dimensional geometry allows the uncollided neutron response to be expressed as a simple exponential attenuation function. For embodiments of the invention requiring a void space measurement, it is further known that the chemical munition 20 is only about 90%+/−0.5% filled with the chemical agent, resulting in a void space within the chemical agent containment area 34, generally filled with air, e.g., an air bubble.

The chemical agent is preferably in a liquid phase and may include, but is not limited to, organo-phosphorus nerve agents, such as agent GA (Tabun) Dimethylphosphoramidocyanidic acid, ethyl ester; agent GB (Sarin) Methylphosphonofluoridic acid (1-methylethyl) ester; agent GD (Soman) Methylphosphonofluoridic acid, 1,2,3-trimethylpropyl ester; Methylphosphonothioic acid, S-[2-(diethylamino)ethyl]O-2-methylpropyl ester; and agent VX Methylphosphonothioic acid, S-[2-[bis(1-methylethyl)amino]ethyl]O-ethyl ester. The uncollided macroscopic neutron cross-sections for various chemical agents at selected neutron energies and/or the linear attenuation coefficients for various chemical agents at selected gamma-ray energies are measured and available, by methods known in the art.

As described in the Background section above, it is known that the probability that a neutron travels a distance $X_C$ through a compound C, without undergoing a neutron-nucleus interaction is described by $e^{-\Sigma_C X_C}$. If a neutron beam passes in series through m successive compounds, then the probability of zero neutron-nucleus interactions occurring over the total path length is given by Equation (3). For the chemical munition 20 shown in FIGS. 1 and 2, the total path length of a radiation transmission through the chemical munition 20 at the selected cross-section 22 includes m=2 successive materials: the steel shell 32 and the chemical agent containment area 34. Equation (4) describes the relationship between the measured uncollided neutron intensity I and the macroscopic neutron cross-section $\Sigma_C$ for compound C—a characteristic unique to compound C and useful for identification purposes.

The attenuation equation, Equation (4), also describes the uncollided gamma-ray intensity from gamma-ray transmissions, except that the variable $\Sigma_C$, the total macroscopic neutron cross-section for compound C, is replaced by the variable $\mu_C$, the linear attenuation coefficient for compound C. Therefore, Equation (4) describes the relationship between the measured uncollided gamma-ray intensity I and the linear attenuation coefficient $\mu_C$ for compound C, also a characteristic unique to compound C and useful for identification purposes.

EMBODIMENT 1

The Two Energy Void/CA Algorithm

In a first embodiment, neutron transmission measurements and a Two Energy Void/CA Algorithm are used to easily identify the chemical agent, based on the assumptions, principles, and chemical munition construction described in the Detailed Description of the Invention above. Two neutron beam energies are selected for conducting the uncollided neutron transmission measurements, in accordance with the apparatus illustrated in FIG. 1. Combinations of the energy pairs are selected, such that a ratio of known macroscopic neutron cross-sections for candidate chemical agents is unique for the chemical agent.

A first set of two neutron transmission measurements is conducted at first and second selected neutron beam energies, by transmitting a neutron beam through the chemical munition 20 along a selected transmission path at a selected cross-section 22, such that the neutron beam passes through the chemical agent containment area 34 containing a void space (air bubble). The uncollided neutron transmission responses at the two selected neutron beam energies are defined by the variables $(I_1, I_2)_{void}$, i.e., the count rate $(I_1)_{void}$ at the first neutron energy and the count rate $(I_2)_{void}$ at the second neutron energy. These measurements are described mathematically by Equations (5) and (6), normalized to the calibration constant K.

$$(I_1)_{VOID} = K_1 e^{-\Sigma_{S1} X_S} e^{-\Sigma_{C1} X_C} \quad (5)$$

$$(I_2)_{VOID} = K_2 e^{-\Sigma_{S2} X_S} e^{-\Sigma_{C2} X_C} \quad (6)$$

where $I_1$ is the count rate at the first neutron energy for the void space, in counts/second;

$I_2$ is the count rate at the second neutron energy for the void space, in countg/second;

$K_1$ is the radiation detector calibration constant for the first neutron energy, in counts/second, known;

$K_2$ is the radiation detector calibration constant for the second neutron energy, in counts/second, known;

$\Sigma_{S1}$ is the macroscopic neutron cross-section through steel at the first neutron energy, either known or measured in $cm^{-1}$;

$\Sigma_{S2}$ is the macroscopic neutron cross-section through steel at the second neutron energy, either known or measured in $cm^{-1}$;

$X_S$ is the path length through the steel shell of the munition in centimeters, unknown;

$X_C$ is the path length through the chemical agent containment area (void space) contained within the munition in cm, unknown;

$\Sigma_{C1}$ is the macroscopic neutron cross-section through the chemical agent containment area (void space) at the first neutron energy, unknown; and $\Sigma_{C2}$ is the macroscopic neutron cross-section through the chemical agent containment area (void space) at the second neutron energy, unknown.

Importantly, since it is assumed that the uncollided neutron transmission through the void space alone results in a neutron transmission measurement approximately equal to 1.0, the uncollided neutron transmission responses $(I_1, I_2)_{void}$ describe the probability of zero neutron-nucleus interactions occurring along the path length of the steel shell only, at the two selected neutron energies. This is more clearly described by rewriting Equations (5) and (6) as Equations (7) and (8), respectively.

$$\left(\frac{I_1}{K_1}\right)_{VOID} = e^{-\Sigma_{S1} X_S} \underbrace{e^{-\Sigma_{C1} X_C}}_{VOID=1} \quad (7)$$

$$\left(\frac{I_2}{K_2}\right)_{VOID} = e^{-\Sigma_{S2} X_S} \underbrace{e^{-\Sigma_{C2} X_C}}_{VOID=1} \quad (8)$$

Next, the chemical munition 20 is re-oriented, preferably by inverting the chemical munition 20, such that the unidentified chemical agent now occupies the volume within the chemical agent containment area 34 of the chemical munition 20 at the selected cross-section 22, previously occupied by the void space. In this way, the neutron transmission measurements performed for the chemical agent have the identical geometry, or path length $X_C$, as the neutron transmission measurements performed for the void space.

A second set of two neutron transmission measurements is conducted for the chemical agent (CA) at the same first and second neutron beam energies as the neutron transmission measurements conducted previously for the void space, by transmitting a neutron beam through the chemical munition 20 along the same selected transmission path, such that the neutron beam passes through the chemical agent containment area 34 containing the chemical agent. The resulting count rate measurements $(I_1, I_2)_{CA}$ are detected at the on-axis neutron detector. The parameters of the neutron transmission measurements for the void spate $(I_1, I_2)_{void}$ and chemical agent $(I_1, I_2)_{CA}$ measurements are constant, except for the orientation of the chemical munition, a modification that does not affect any path length parameters.

The Two Energy Void/CA Algorithm is applied to formulate a first ratio of the void space uncollided neutron transmission measurement at the first energy to the chemical agent uncollided neutron transmission measurement at the first energy, and a second ratio of the void space uncollided neutron transmission measurement at the second energy to the chemical agent uncollided neutron transmission measurement at the second energy, such that the contribution of the uncollided neutron transmission through the steel shell only is effectively eliminated from both ratios, assuming the uncollided neutron transmission through the void space is nearly 1.0 counts/second. The next step of the algorithm involves formulating a third ratio of the first ratio to the second ratio, or a ratio of the macroscopic neutron cross-section ratio for the uncollided neutron transmission for the chemical agent only at the first energy to the macroscopic neutron cross-section for the uncollided neutron transmission for the chemical agent only at the second energy. These steps of the algorithm are applied as follows.

The first ratio and second ratios are described by Equations (9) and (10), as the natural logs of the ratios of the void space uncollided neutron transmission measurements $(I_1, I_2)_{void}$ to the chemical agent uncollided neutron transmission measurements $(I_1, I_2)_{CA}$ at the first and second neutron energies.

$$\ln\left(\frac{\left(\frac{I_1}{K_1}\right)_{void}}{\left(\frac{I_1}{K_1}\right)_{CA}}\right) = \Sigma_{C1} X_C \quad (9)$$

$$\ln\left(\frac{\left(\frac{I_2}{K_2}\right)_{void}}{\left(\frac{I_2}{K_2}\right)_{CA}}\right) = \Sigma_{C2} X_C \quad (10)$$

Equations (9) and (10) individually represent the product of the macroscopic neutron cross-section at the selected energy and the path length of the neutron transmission through the chemical agent containment area.

Equation (11) describes the third ratio, the ratio of Equation (9) to Equation (10), representing the final result—the estimated ratio of the chemical agent macroscopic neutron cross-sections at the first and second energies.

$$\frac{\ln\left[\frac{\left(\frac{I_1}{K_1}\right)_{VOID}}{\left(\frac{I_2}{K_2}\right)_{CA}}\right]}{\ln\left[\frac{\left(\frac{I_2}{K_2}\right)_{VOID}}{\left(\frac{I_2}{K_2}\right)_{CA}}\right]} = \frac{\sum_{C1} X_C}{\sum_{C2} X_C} = \frac{\sum_{C1}}{\sum_{C2}} \qquad (11)$$

Since macroscopic neutron cross-sections at selected energies are unique to chemical agents, a ratio of macroscopic neutron cross-sections at two selected energies is similarly useful for identifying the contained chemical agent. Known macroscopic neutron cross-section values for candidate chemical agents at the selected first and second neutron energies are used to calculate the ratio described by Equation (11), and the target chemical agent contained within the chemical munition 20 is identified by determining which candidate chemical agent produces the closest match. Preferably, a candidate chemical agent database and other computerized systems are configured for the easy selection of candidate chemical agents, calculation of the required ratios, comparison of calculated muid measured ratios, and identification of the chemical agent.

Table III below lists examples of macroscopic neutron cross-section values for selected chemical agents at various neutron energies for a 155 mm chemical ordnance obtained from radiation transport calculations executed in accordance with the Monte Carlon-Particle transport code (MCNP) for simulating the transport of neutrons.

TABLE III

Total of Neutron Attenutaion (I/K) for the Chemical Agents and Steel Only at Various Energy Levels

| A-gent | Energy Levels, Mev | | | | | | |
|---|---|---|---|---|---|---|---|
| | 0.0275 | 0.050 | 0.100 | 0.430 | 1.172 | 1.372 | 2.75 |
| Steel | 1.002 | 0.419 | 0.383 | 0.319 | 0.189 | 0.135 | 0.256 |
| GA | 7.2e-7 | 7.6e-6 | 3.5e-5 | 9.3e-4 | 2.36e-2 | 3.75e-2 | 5.72e-2 |
| GB | 6.3e-7 | 7.1e-6 | 3.3e-5 | 9.0e-4 | 2.34e-2 | 3.71e-2 | 5.72e-2 |
| GD | 2.7e-7 | 3.0e-6 | 1.6e-5 | 5.5e-4 | 1.79e-2 | 2.93e-2 | 4.83e-2 |
| VX | 3.0e-9 | 3.8e-8 | 3.6e-7 | 4.6e-5 | 4.93e-3 | 8.96e-3 | 2.13e-2 |

Embodiment 1 Adapted to Gamma-ray Measurement Transmissions

The first embodiment of the present method is also valid for non-interacting photon measurements, wherein a gamma beam is used to interrogate the chemical munition 20, rather than neutron transmissions. FIG. 2 illustrates the apparatus appropriate for practicing the present embodiment, which is based on the assumptions, principles, and chemical munition construction described in the Detailed Description of the Invention above. Two gamma-ray beam energies are selected for conducting the non-interacting photon transmission measurements.

A first set of two gamma-ray transmission measurements is conducted at the first and second selected gamma-ray beam energies, by passing a gamma-ray beam through the chemical agent 20 along a selected transmission path at a selected cross-section 22, such that the gamma-ray beam passes through the chemical agent containment area 34 containing a void space, and by detecting the corresponding non-interacting photon transmission responses. Next, the chemical munition 20 is re-oriented, such that the chemical agent now occupies the volume within the chemical agent containment area 34 previously occupied by the void space. A second set of two gamma-ray transmission measurements are conducted along selected transmission path through the chemical munition 20, including transmission through the chemical agent, at the same first and second gamma beam energies.

The gamma linear attenuation coefficient ($\mu_i$) for the selected first and second energies, $e_i$, comprises the ratio for identifying the chemical agent, rather than the macroscopic neutron cross-sections described above. The gamma linear attenuation coefficient is a function of the chemical agent molecular structure and the gamma photon energy. For a single photon energy, the gamma linear attenuation coefficient at a selected energy is related to the count rate through the liquid chemical agent and the count rate through the gas (void space) by Equation (12).

$$\ln\left(\frac{N_g}{N_f}\right) = \mu_f x \qquad (12)$$

where $N_g$ is the count rate through the gas, or void space;
$N_f$ is the count rate through the liquid chemical agent;
$\mu_f$ is the gamma linear attenuation coefficient for the gamma at the selected energy; and
x is the path length through the liquid/gas space.

Assuming two different photon energy gamma rays are detectable, the ratio $Q(e_1, e_2)$ of the linear attenuation coefficients at the selected first and second energies $e_1$, $e_2$ identifies the chemical agent, as expressed in Equation (13).

$$Q(e_1, e_2) = \frac{\ln\left(\frac{N_g(e_1)}{N_f(e_1)}\right)}{\ln\left(\frac{N_g(e_2)}{N_f(e_2)}\right)} = \frac{\mu_f(e_1)x}{\mu_f(e_2)x} = \frac{\mu_f(e_1)}{\mu_f(e_2)} \qquad (13)$$

Known gamma-ray linear attenuation coefficients for candidate chemical agents at the selected first and second gamma-ray energies are used to calculate the ratio described by Equation (13), and the target chemical agent contained within the chemical munition 20 is identified by determining which candidate chemical agent produces the closest match.

Advantageously, this embodiment relies on non-interaction of the gamma beam over a measured path length that is ultimately eliminated from the identification ratio, such that the existence of localized abnormalities, e.g., surface corrosion, do not affect the accuracy of the measurement.

EMBODIMENT 2

The Two Energy CA Algorithm

In a second embodiment, a Two Energy CA Algorithm is applied, such that neutron transmission measurements through a void space and rotation of the chemical agent are not required. The Two Energy CA Algorithm utilizes the total path length relationship to eliminate unknown variables to derive a minimization formula having a solution that identifies the chemical agent. The present embodiment is based on the assumptions, principles, and chemical munition construction described in the Detailed Description of the Invention above. First and second neutron beam energies are selected for conducting the uncollided neutron transmission measurements.

Two neutron transmission measurements are conducted at the first and second neutron energies, by passing a neutron beam through a selected transmission path at a selected cross-section 22 of the chemical munition 20, such that the neutron beam passes through the steel shell 32 and the chemical agent containment area 34 containing the chemical agent (CA). The resulting uncollided neutron measurements are described by Equations (14) and (15).

$$\left(\frac{I_1}{K_1}\right) = e^{-\Sigma_{S1} X_S} e^{-\Sigma_{C1} X_C} \quad (14)$$

$$\left(\frac{I_2}{K_2}\right) = e^{-\Sigma_{S2} X_S} e^{-\Sigma_{C2} X_C} \quad (15)$$

where $I_1$ is the count rate at the first neutron energy for the chemical munition, in counts/second;

$I_2$ is the count rate at the second neutron energy for the chemical munition, in counts/second;

$K_1$ is the radiation detector calibration constant for the first neutron energy, in counts/second, known;

$K_2$ is the radiation detector calibration constant for the second neutron energy, in counts/second, known;

$\Sigma_{S1}$ is the macroscopic neutron cross-section through steel at the first neutron energy, either known or measured in $cm^{-1}$;

$\Sigma_{S2}$ is the macroscopic neutron cross-section through steel at the second neutron energy, either known or measured in $cm^{-1}$;

$\Sigma_{C1}$ is the macroscopic neutron cross-section through the chemical agent within the containment area at the first neutron energy, unknown;

$\Sigma_{C2}$ is the macroscopic neutron cross-section through the chemical agent within the containment area at the second neutron energy, unknown;

$X_S$ is the path length through the steel shell of the munition in centimeters, unknown; and $X_C$ is the path length through the chemical agent within the containment area in cm, unknown, Variables $C_1$ and $C_2$ are next defined in terms of the natural log of Equations (14) and (15).

$$C_1 = \ln\frac{K_1}{I_1} \quad (16)$$

$$C_1 = \ln\frac{K_2}{I_2} \quad (17)$$

Given the total path length relationship $D=X_S+X_C$, Equations (14), (15), (16), and (17) are combined in Equation (18).

$$\begin{bmatrix} \Sigma_{S1} & \Sigma_{C1} \\ \Sigma_{S2} & \Sigma_{C2} \end{bmatrix} \begin{bmatrix} X_S \\ X_C \end{bmatrix} = \begin{bmatrix} C_1 \\ C_2 \end{bmatrix} \quad (18)$$

The solution for Equation (18) is expressed by Equations (19) and (20).

$$X_S = \frac{\Sigma_{C2} C_1 - \Sigma_{C1} C_2}{\Sigma_{S1} \Sigma_{C2} - \Sigma_{S2} \Sigma_{C1}} \quad (19)$$

$$X_C = \frac{\Sigma_{S1} C_2 - \Sigma_{S2} C_1}{\Sigma_{S1} \Sigma_{C2} - \Sigma_{S2} \Sigma_{C1}} \quad (20)$$

Substituting the terms of Equations (19) and (20) into the total path length equation $D=X_S+X_C$ results in Equation (21).

$$D = \frac{\Sigma_{C2} C_1 - \Sigma_{C1} C_2}{\Sigma_{S1} \Sigma_{C2} - \Sigma_{S2} \Sigma_{C1}} + \frac{\Sigma_{S1} C_2 - \Sigma_{S2} C_1}{\Sigma_{S1} \Sigma_{C2} - \Sigma_{S2} \Sigma_{C1}} \quad (21)$$

Equation (21) is rewritten in a simplified form as Equation (22).

$$\Sigma_{C2}(C_1 - D\Sigma_{S1}) - \Sigma_{C1}(C_2 - D\Sigma_{S2}) = \Sigma_{S2} C_1 - \Sigma_{S1} C_2 \quad (22)$$

All variables in Equation (22) are known, with the exception of $\Sigma_{C1}$, $\Sigma_{C2}$, the macroscopic neutron cross-section measurements through the chemical agent at the first and second neutron energies. Known pairs of macroscopic neutron cross-sections for a candidate chemical agents at the two selected neutron energies are used to solve Equation (22). Preferably, the related minimization formula, Equation (23), easily determines the optimum candidate, by successively evaluating candidate chemical agents and their corresponding macroscopic neutron cross-sections, $\Sigma_{C1}$, $\Sigma_{C2}$, to determine the chemical agent exhibiting the closest fit.

$$\text{Err} = \Sigma_{C2}(C_1 - D\Sigma_{S1}) - \Sigma_{C1}(C_2 - D\Sigma_{S2}) - \Sigma_{S2} C_1 + \Sigma_{S1} C_2 \quad (23)$$

A database of candidate chemical agents and computerized systems may easily be configured to solve Equation (23).

For first and second neutron energies of 0.0275 Mev and 1.372 MeV, Table IV below provides error information for simulations for identifying the chemical agents GA, GB, GD, and VX, in accordance with Equations (22) and (23).

TABLE IV

Estimated Error for Two Energy CA Algorithm Fit to MCNP Data

| CHEMICAL | ERROR | CHEMICAL | ERROR |
|---|---|---|---|
| GA Simulation | | VX Simulation | |
| GA | 3.03e-4 | GA | 7.57e-1 |
| GB | -1.78e-2 | GB | 7.26e-1 |
| GD | -1.35e-1 | GD | 6.14e-1 |
| VX | -7.57e-1 | VX | -1.79e-3 |
| GB Simulation | | GD Simulation | |
| GA | 1.79e-2 | GA | 1.35e-1 |
| GB | -2.34e-4 | GB | 1.15e-1 |
| GD | -1.15e-1 | GD | -4.72e-4 |
| VX | -7.27e-1 | VX | -6.17e-1 |

Embodiment 2 Adapted to Gamma-ray Measurement Transmissions

The second embodiment is also valid for gamma beam transmissions and the detection of non-interacting photons, based on the assumptions, principles, and chemical munition construction described in the Detailed Description of the Invention above. Two gamma-ray beam energies are selected for conducting the non-interacting photon transmission measurements.

Two gamma transmission measurements are conducted at the first and second selected neutron energies, by passing a gamma beam through a selected transmission path at a selected cross-section 22 of the chemical munition 20, such that the gamma beam passes through the steel shell 32 and the chemical agent containment area 34 containing the chemical agent (CA). The Two Energy CA Algorithm is applied as above, except that the detected count rates $I_1$ and $I_2$ are for non-interacting photons, and $\Sigma_x$ is replaced by corresponding linear attenuation coefficients $\mu_x$. Given the total path length relationship $D=X_S+X_C$, all variables in Equation (24) are known, with the exception of $\mu_{C1}, \mu_{C2}$, the lines attenuation coefficients.

$$\mu_{C2}(C_1-D\mu_{S1})-\mu_{C1}(C_2-D\mu_{S2})=\mu_{S2}C_1-\mu_{S1}C_2 \quad (24)$$

Pairs of known linear attenuation coefficient values for candidate chemical agents at the two selected neutron energies are used to solve Equation (23). Minimization formula, Equation (25) more easily determines the optimum candidate chemical agent exhibiting the closest fit.

$$\text{Err}=\mu_{C2}(C_1-D\mu_{S1})-\mu_{C1}(C_2-D\mu_{S2})-\mu_{S2}C_1+\mu_{S1}C_2 \quad (25)$$

Preferably, a database of candidate chemical agents and computerized systems may easily be configured to solve Equation (25).

EMBODIMENT 3

The Modified Two Energy CA Algorithm

In a third embodiment, a Modified Two Energy CA Algorithm is used to identify the contained chemical agent by utilizing the total path length relationship to estimate a ratio of relative macroscopic neutron cross-sections, compensated by known characteristics of the steel shell. The present embodiment is based on the assumptions, principles, and chemical munition construction described in the Detailed Description of the Invention above.

Two uncollided neutron transmission measurements, resulting in count rates $I_1$ and $I_2$, are conducted at first and second selected neutron energies, by passing a neutron beam through a selected transmission path at a selected cross-section 22 of the chemical munition 20, such that the neutron beam passes through the steel shell 32 and the chemical agent containment area 34 containing the chemical agent (CA). The Modified Two Energy CA Algorithm is applied to estimate a ratio of relative macroscopic neutron cross-sections for the chemical agent at the two selected energies, $\delta\Sigma_{ci}$, in reference to the macroscopic neutron cross-section of the steel. Pquations (26) and (27) describe the uncollided neutron transmission response.

$$I_1=K_1 e^{-\Sigma_{S1}X_S} e^{-\Sigma_{C1}X_C} \quad (26)$$

$$I_2=K_2 e^{-\Sigma_{S2}X_S} e^{-\Sigma_{C2}X_C} \quad (27)$$

Given the total path length relationship $D=X_S+X_C$, and as expressed by Equations (16) and (17), C1 and C2 are defined by Equations (28) and (29).

$$C_1 = \ln\frac{K_1}{I_1} \quad (28)$$

$$C_1 = \ln\frac{K_2}{I_2} \quad (29)$$

Combining Equations (26), (27), (28), and (29) results in Equations (30) and (31).

$$C_1=\Sigma_{S1}(D-X_C)+\Sigma_{C1}X_C \quad (30)$$

$$C_2=\Sigma_{S2}(D-X_C)+\Sigma_{C2}X_C \quad (31)$$

Equations (30) and (31) are combined into Equation (32).

$$\frac{C_1-\Sigma_{S1}D}{C_2-\Sigma_{S2}D}=\frac{\Sigma_{C1}-\Sigma_{S1}}{\Sigma_{C2}-\Sigma_{S2}} \quad (32)$$

Since the macroscopic neutron cross-section for steel $\Sigma_{si}$ is known at energy i, the relative macroscopic neutron cross-section for the chemical agent referenced to the steel is described by Equations (33) and (34).

$$\delta\Sigma_{Ci}=\Sigma_{Ci}-\Sigma_{Si} \quad (33)$$

$$\frac{C_1-\Sigma_{S1}D}{C_2-\Sigma_{S2}D}=\frac{\delta\Sigma_{C1}}{\delta\Sigma_{C2}} \quad (34)$$

The ratio of the relative macroscopic neutron cross-sections for the chemical agent at the first and second neutron energies is unique for each chemical agent. Therefore, as in the first embodiment, known macroscopic neutron cross-section values for candidate chemical agents at the first and second neutron energies, together with the known macroscopic neutron cross-section of steel at the first and second energies, are to calculate the ratio expressed by Equation (34) and determine the closest match, thereby identifying the contained chemical agent.

Embodiment 3 Adapted to Gamma-ray Measurement Transmissions

The third embodiment of the present method is valid for non-interacting photon measurements, wherein a gamma beam is used to interrogate the target material, rather than the neutron transmissions, in view of the assumptions, principles, and chemical munition construction described in the Detailed Description of the Invention above.

Two gamma transmission measurements, resulting in count rates $I_1$ and $I_2$, are conducted at first and second selected gamma energies, by passing a gamma beam through a selected transmission path at a selected cross-section 22 of the chemical munition 20, such that the gamma beam passes through the steel shell 32 and the chemical agent containment area 34 containing the chemical agent (CA). The above described Modified Two Energy CA Algorithm is applied to estimate a ratio of relative linear attenuation coefficients for the chemical agent at the two selected energies, $\delta\mu_{ci}$, in reference to the linear attenuation coefficient of the steel. Equation (35) below describes the relative linear attenuation coefficient ratio for the chemical agent.

$$\frac{C_1-\mu_{S1}D}{C_2-\mu_{S2}D}=\frac{\delta\mu_{C1}}{\delta\mu_{C2}} \quad (35)$$

The ratio of the relative linear attenuation coefficients described by Equation (35) is unique for each chemical agent, and known linear attenuation coefficients for candidate chemical agents at the first mid second gamma-ray energies, together with the known linear coefficient of steel at the first and second gamma-ray energies, are used to calculate the ratio described by Equation (35), and the contained chemical agent is identified by determining a calculated ratio most closely approximating the measured ratio.

EMBODIMENT 4

The High Precision Two Energy Algorithm

In a fourth embodiment, also based on the assumptions, principles, and chemical munition construction described in the Detailed Description of the Invention above, a High Precision Two Energy Algorithm is used to identify the contained chemical agent, especially for applications where insufficient differences exist between the macroscopic neutron cross-sections of candidate chemical agents for the accurate identification of the contained chemical agent by any of the previous embodiments. In this embodiment, uncollided neutron transmission measurements are conducted at first and second base neutron energies ($\epsilon_0$), and at first and second perturbated neutron energies ($\epsilon_0+\delta\epsilon$). The High Precision Two Energy CA Algorithm, which is the Two Energy CA Algorithm of the second embodiment of the invented method augmented with Taylor geries concepts, is applied to more precisely approximate the identity of the contained chemical agent, than is probable by applying the Two Energy CA Algorithm alone. Therefore, first and second base neutron beam energies are selected for conducting the uncollided neutron transmission measurements required by the present embodiment.

The first set of uncollided neutron transmission measurements involves measuring the uncollided neutron transmission of a mono-energetic neutron beam through a selected transmission path at a selected cross-section 22 of the chemical munition 20, including the steel shell and chemical agent, at the first base neutron energy ($\epsilon_1$) and at the first perturbated neutron energy ($\epsilon_1+\delta\epsilon$). For example, if 250 keV is selected as the first neutron energy, an uncollided neutron transmission measurement is first detected at a neutron beam energy of 250 keV. Next, the voltage of the proton accelerator is slightly adjusted, such that the first neutron energy is perturbed to 255 keV, and a second uncollided neutron transmission measurement is detected at a neutron beam energy of 255 keV.

A second set of uncollided neutron transmission measurements is conducted for measuring the uncollided neutron transmission of a mono-energetic neutron beam through the same selected transmission path at the same selected cross-section 22 of the chemical munition 20, including the steel shell and chemical agent, at the second base neutron energy ($\epsilon_2$) and at the second perturbated neutron energy ($\epsilon_2+\delta\epsilon$).

Equations (36) and (37) describe the measured uncollided neutron transmission measurements for the base and perturbated neutron energies.

$$I(\varepsilon_o) = K(\varepsilon_o)e^{-\Sigma_{S\varepsilon_o} X_S - \Sigma_{C\varepsilon_o} X_C} \quad (36)$$

$$I(\varepsilon_o + \delta\varepsilon) = K(\varepsilon_o + \delta\varepsilon)e^{-\Sigma_{S\varepsilon_o+\delta\varepsilon} X_S - \Sigma_{C\varepsilon_o+\delta\varepsilon} X_C} \quad (37)$$

Assuming that the calibration of the proton accelerator and the detector system do not shift between the base neutron energies ($\epsilon_0$) and the perturbated neutron energies ($\epsilon_0+\delta\epsilon$), such that $K(\epsilon_0)=K(\epsilon_0+\delta\epsilon)$, the natural log of the ratio of Equations (36) and (37) is described by Equation (38).

$$\ln\left(\frac{I(\varepsilon_o)}{I(\varepsilon_o + \delta\varepsilon)}\right) = (\Sigma_{S\varepsilon_o+\delta\varepsilon} - \Sigma_{S\varepsilon_o})X_S + (\Sigma_{C\varepsilon_o+\delta\varepsilon} - \Sigma_{C\varepsilon_o})X_C \quad (38)$$

The Taylor Series is used to approximate the macroscopic cross-sections of the steel and chemical agent, individually, at the first and second perturbated neutron energies, as described by Equations (39) and (40), respectively.

$$\sum_{S\varepsilon_o+\delta\varepsilon} = \sum_{S\varepsilon_o} + \frac{\partial \sum_{S\varepsilon_o}}{\partial \varepsilon} \frac{\delta\varepsilon}{N_{S\varepsilon_o}} \quad (39)$$

$$\sum_{C\varepsilon_o+\delta\varepsilon} = \sum_{C\varepsilon_o} + \frac{\partial \sum_{C\varepsilon_o}}{\partial \varepsilon} \frac{\delta\varepsilon}{N_{C\varepsilon_o}} \quad (40)$$

Assuming the total path length relationship, $D=X_S+X_C$, Equations (38), (39), and (40) are combined in Equations (41).

$$\frac{\ln\left(\frac{I(\varepsilon_o)}{I(\varepsilon_o+\delta\varepsilon)}\right)}{\delta\varepsilon} = DC(\varepsilon_o) = M_{S\varepsilon_o}X_S + M_{C\varepsilon_o}X_C \quad (41)$$

Also, the natural log of Equation (36) is described by Equation (42).

$$\ln\left(\frac{K(\varepsilon_o)}{I(\varepsilon_o)}\right) = C(\varepsilon_o) = \sum_{S\varepsilon_o} X_S + \sum_{C\varepsilon_o} X_C \quad (42)$$

From the above, the following system of three equations is derived.

$$C(\epsilon_0)=\Sigma_{s\epsilon_0}X_S+X_{C\epsilon_0}X_C \quad (43)$$

$$DC(\epsilon_0)=M_{s\epsilon_0}X_S+M_{C\epsilon_0}X_C \quad (44)$$

$$D=X_S+X_C \quad (45)$$

Since the four variables, $X_S$, $X_C$, $M_{c\epsilon0}$, and $\Sigma_{c\epsilon0}$, are unknown, the above system of equations is only reducible to an expression involving two unknowns of interest, namely $M_{c\epsilon0}$, and $\Sigma_{c\epsilon0}$, expressed in Equation (46).

$$(\Sigma_{C\epsilon_0}-\Sigma_{S\epsilon_0})(DC(\epsilon_0)-M_{S\epsilon_0}D)=(M_{C\epsilon_0}-M_{S\epsilon_0})(C(\epsilon_0)-\Sigma_{S\epsilon_0}D) \quad (46)$$

Equation (46) is rewritten as an error minimization formula, Equation (47).

$$\text{Err}(\epsilon_0)=(\epsilon_{C\epsilon0}-\Sigma_{S\epsilon0})(DC(\epsilon_0)-M_{S\epsilon0}D)-(M_{C\epsilon0}-M_{s\epsilon0})(C(\epsilon_0)-\Sigma_{S\epsilon0}D) \quad (47)$$

The uncollided neutron measurements for the first base energy and the first perturbated energy, and the uncollided neutron measurements for the second base energy and the second perturbated energy are successively inserted into the error minimization formula, and a database of known macroscopic neutron cross sections at the base and perturbated first and second neutron energies is used to determine a best fit, thereby identifying the contained material.

The above derived High Precision Two Energy Algorithm is more distinguishing than the algorithms previously described, in that it requires fitting the algorithm to four points (the chemical agent macroscopic cross-section and the slope of the cross-section to energy at the two neutron energies).

Although the embodiments of the present invention include the application of specific algorithms to neutron transmission measurements and their corresponding macro neutron cross-section ratios, and also to gamma bea transmission measurements and their corresponding linear attenuation ratios, the neutron transmission measurements are preferred where high energy photon beams are required to penetrate the container enclosing the chemical agent, such that sensitivity of the non-interacting transmission photons to the chemical agent is significantly decreased.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. While the invention has been described with reference to details of the illustrated embodiment, these details are not intended to limit the scope of the invention, rather the scope of the invention is to be defined by the claims appended hereto.

What is claimed is:

1. A method for non-intrusively identifying a target material enclosed within a container, comprising the steps of:

measuring a total path length for a beam of radiation transmitted through the container enclosing the target material, along a selected, essentially linear transmission path, such that the measured total path length is approximately equal to an unknown path length of the beam through the container plus an unknown path length of the beam through the enclosed target material, referred to as the total path length relationship;

transmitting a first beam of mono-energetic gamma radiation having a first energy through the container and target material along the selected transmission path, and measuring a first count rate of uncollided, unscattered gamma radiation transmitted through the container and target material, with an on-axis detector aligned with the selected transmission path;

transmitting a second beam of mono-energetic radiation having a second energy through the container and target material along the selected transmission path, and measuring a second count rate of uncollided, unscattered gamma radiation transmitted through the container and target material, with the on-axis detector aligned with the transmission path;

applying an algorithm to determine an estimated first relative and an estimated second relative linear attenuation coefficient for the chemical agent exposed to the first and second gamma radiation energies respectively and calculating a ratio of the first estimated relative linear attenuation coefficient to the second estimated relative linear attenuation coefficient; and identifying the target material by comparing the calculated ratio with a known linear relative attenuation ratio unique to candidate target materials and thus, determining the candidate target material.

2. The method according to claim 1, wherein the beam of radiation is a gamma-ray beam, the uncollided radiation particles are photons, and the parameter is a gamma-ray linear attenuation coefficient.

3. The method according to claim 1, wherein the algorithm rules for determining the respective relative linear attenuation coefficients and formulating the identifying relative ratio, comprise the steps of:

formulating a first expression which is a function of a calibration constant for a detection device at the first energy level and of a count rate at the first energy level;

formulating a second expression which is a function of the calibration constant for the detector at the second energy level and of the count rate at the second energy level;

determining a total path length;

establishing a first energy linear attenuation coefficient for a metal casing enclosing a unknown compound at the first energy level and establishing a second energy linear attenuation coefficient for the metal casing at the second energy level;

employing an second algorithm to determine a first relative linear coefficient at the first energy level and using the same second algorithm to determine a second relative linear coefficient at the second energy level; and formulating the identifying relative ratio as a ratio of the first relative linear coefficient to the second relative linear coefficient;

comparing the calculated relative ratio to a set of known measured ratios to determine the encapsulated material.

4. The method according to claim 1, wherein the target material is a liquid.

5. The method according to claim 1, wherein the target material is a chemical agent selected from the group consisting of Agent GA described as Dimethylphosphoramidocyanidic acid, ethyl ester; Agent GB described as Methylphosphonofluoridic acid (1-methylethyl) ester; and Agent GD described as Methylphosphonofluoridic acid, 1,2,3-trimethylpropyl ester; Agent VX described as Methylphosphonothioic acid, S-[2-(diethylamino)ethyl]O-2-methylpropyl ester; Agent H described as 1,1'Thiobis[2-chloroethane]; Agent L described as (2-Chloroethenyl) arsonous dichloride; and Agent T bis(2(2-chloroethylthio) ethyl) ester.

6. The method according to claim 1, wherein the container is comprised of steel.

7. The method according to claim 1, wherein the beams of radiation have energies in the range of between about 100 keV and about 1000 keV.

8. The method according to claim 1, wherein the steps of applying the algorithm and identifying the contained target material include utilizing a computer program and a computer database of candidate target material parameter values.

9. The method of claim 1 where said first and said second count rate are measured using a a scintillation detector as said on-axis detector.

* * * * *